(12) United States Patent
Hearn et al.

(10) Patent No.: US 9,320,299 B2
(45) Date of Patent: Apr. 26, 2016

(54) SIMULATED SMOKING DEVICE

(75) Inventors: Alex Hearn, London (GB); Richard Mathias, Royston (GB)

(73) Assignee: Kind Consumer Limited, London (GB)

( * ) Notice: Subject to any disclaimer, the term of this patent is extended or adjusted under 35 U.S.C. 154(b) by 926 days.

(21) Appl. No.: 13/577,232

(22) PCT Filed: Feb. 4, 2011

(86) PCT No.: PCT/GB2011/000151
§ 371 (c)(1),
(2), (4) Date: Oct. 23, 2012

(87) PCT Pub. No.: WO2011/095781
PCT Pub. Date: Aug. 11, 2011

(65) Prior Publication Data
US 2013/0037042 A1   Feb. 14, 2013

(30) Foreign Application Priority Data
Feb. 5, 2010   (GB) .................................. 1001944.6

(51) Int. Cl.
| | |
|---|---|
| *A24F 15/12* | (2006.01) |
| *A24F 15/14* | (2006.01) |
| *A24F 47/00* | (2006.01) |
| *A61M 15/06* | (2006.01) |
| *A24F 17/00* | (2006.01) |

(52) U.S. Cl.
CPC .............. *A24F 47/002* (2013.01); *A24F 15/12* (2013.01); *A24F 15/14* (2013.01); *A61M 15/06* (2013.01); *A24F 17/00* (2013.01); *A61M 2209/045* (2013.01); *A61M 2209/06* (2013.01)

(58) Field of Classification Search
CPC ......... A24F 15/12; A24F 17/00; A24F 15/14; A24F 47/00; A24F 47/002
See application file for complete search history.

(56) References Cited

U.S. PATENT DOCUMENTS

| | | | | |
|---|---|---|---|---|
| 2,005,557 | A | * | 6/1935 | Penney .......................... 221/149 |
| 2,251,138 | A | * | 7/1941 | Knight .......................... 292/128 |
| 2,568,151 | A | * | 9/1951 | Hagerty et al. ................ 312/242 |
| 2,626,613 | A | * | 1/1953 | Glance ........................... 131/174 |

(Continued)

FOREIGN PATENT DOCUMENTS

| | | |
|---|---|---|
| EP | 1053955 A2 | 11/2000 |
| JP | S43-20558 Y | 8/1968 |
| WO | 2009001078 A2 | 12/2008 |

(Continued)

OTHER PUBLICATIONS

Notification of Refusal from JPO of 2012-551676, machine english trasnlation, Dec. 25, 2014.*

(Continued)

*Primary Examiner* — Anthony Calandra
(74) *Attorney, Agent, or Firm* — Patterson & Sheridan, L.L.P.

(57) ABSTRACT

A simulated smoking device comprising a simulated cigarette having a cigarette-like shape and a refill device. A drawer is provided in the side of the refill device with a recess for the simulated cigarette. A resilient member biases the drawer open to allow access to the simulated cigarette. A latch is releasable by an inward movement of the drawer whereupon the drawer is unlatched and urged by the resilient member to the open position. The latch is automatically engageable upon closure of the drawer to hold the drawer in a closed position against the action of the resilient member.

10 Claims, 7 Drawing Sheets

(56) References Cited

U.S. PATENT DOCUMENTS 6,065,626 A     5/2000  Huang et al.
2011/0180433 A1*  7/2011  Rennecamp ............... 206/268

FOREIGN PATENT DOCUMENTS

WO      2011015825  A1    2/2011
WO      2011015826  A1    2/2011

OTHER PUBLICATIONS

Certified English Translation of JP 43020558 U Ikeda, patent date 1968, English translation date Jul. 30, 2015.*
International Search Report and Written Opinion for International Application PCT/GB2011/000151 dated Apr. 19, 2011.

* cited by examiner

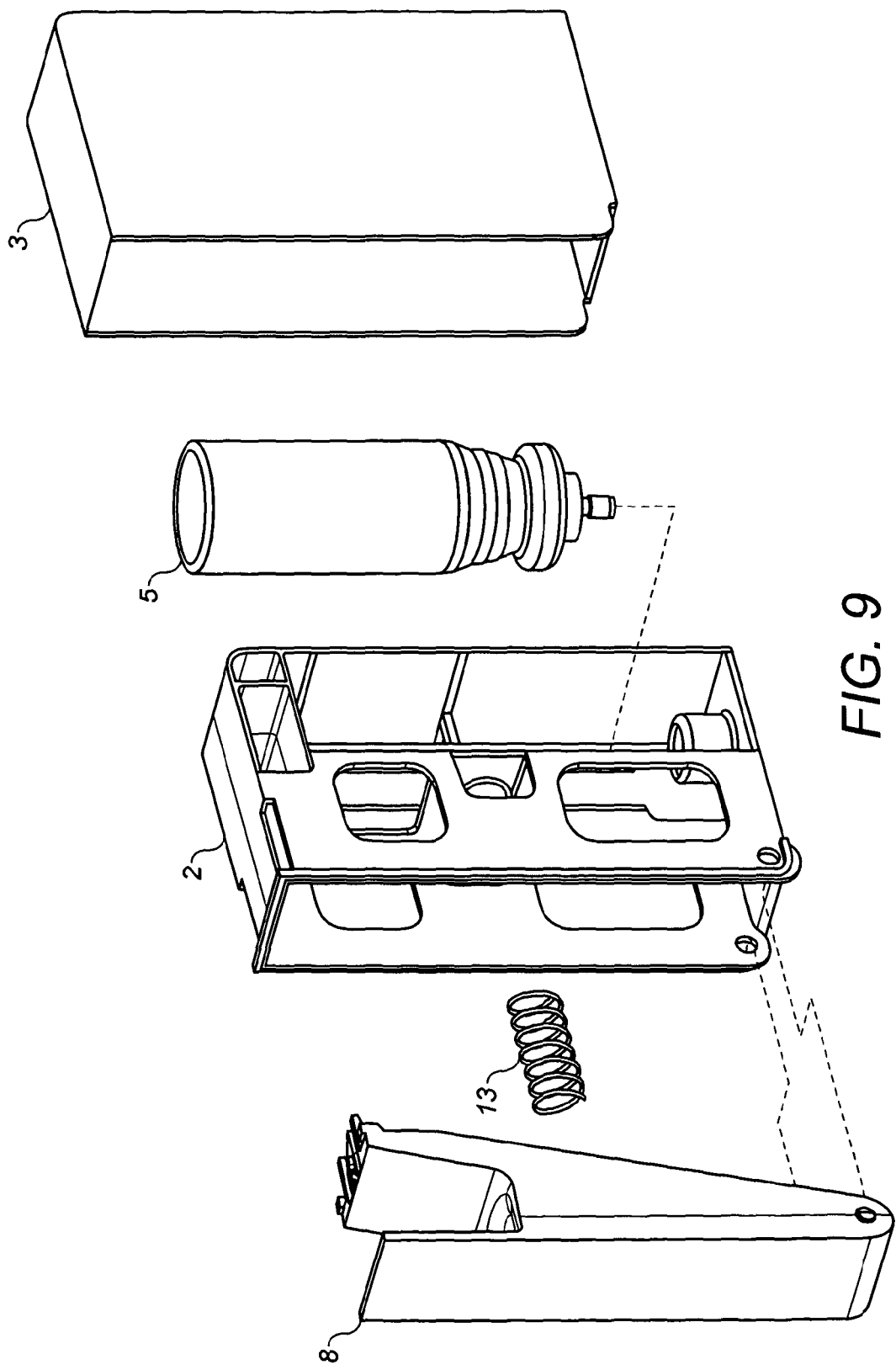

SIMULATED SMOKING DEVICE

The present invention relates to a simulated smoking device comprising a simulated cigarette having a substantially cigarette-like shape and a refill device, the refill device containing a canister of refill gas and having an outlet valve in its bottom surface against which the simulated cigarette is arranged to be pressed to release gas from the canister into the simulated cigarette. Such a device will subsequently be referred to as being "of the kind described".

A device of the kind described is disclosed in our earlier application WO 2009/001078. In this device, the refill pack has a shape corresponding to the shape of a standard cigarette pack. The simulated cigarette is retained within the refill device and a hinged lid is provided in the top corner of the device to provide access to the simulated cigarette. The pack was designed in this way so as to resemble as closely as possible the act of opening a real cigarette pack to remove a real cigarette. However, the disclosure does not address the issue of ease of use of the refill device.

According to the present invention, a simulated smoking device of the kind described is characterised by:
a drawer in the side of the refill device;
a recess within the drawer to retain the simulated cigarette;
a resilient member to bias the drawer into an open position to allow access to the simulated cigarette; and
a latch being releasable by an inward movement of the drawer, whereupon the drawer is unlatched and urged by the resilient member to the open position, and the latch being automatically engagable upon closure of the drawer to hold the drawer in a closed position against the action of the resilient member.

With such an arrangement, a user wishing to use the simulated cigarette simply has to push the drawer inwardly, whereupon the drawer is pushed open by the resilient member presenting the simulated cigarette to the user allowing them to readily remove it. Thus, the user can easily hold the refill device and open the drawer with one hand. They then have a second hand free to remove the simulated cigarette, and press it against the outlet valve in order to fill the simulated cigarette with a charge of gas from the canister. This is a significant improvement on the previous design where it was awkward to hold the refill device and open the hinged lid with a single hand. Users therefore generally tried to do this with two hands which then made the subsequent refill process awkward. Therefore, although the present invention does not mimic the act of opening a conventional cigarette pack in the same manner as WO 2009/061078, this disadvantage is outweighed by the ease of use provided by the opening mechanism.

The drawer may be arranged to slide laterally out of the refill device. However, preferably, the drawer is pivotally mounted about a bottom corner of the refill device. A pivotally mounted device is easier to configure, and can be more reliably operated than a sliding drawer.

The latch may be any suitable type, for example, magnetic or electromagnetic, but preferably has a mechanical interface with the drawer to hold the drawer in the latched position.

The present invention also extends to a refill device for a simulated smoking device, the refill device containing a canister of refill gas, and having an outlet valve in its bottom surface against which a simulated cigarette is arranged, in use, to be pressed to release gas from the canister into the simulated cigarette; characterised by:
a drawer in the side of the refill device;
a recess within the drawer to retain the simulated cigarette, in use;
a resilient member to bias the drawer into an open position to allow access to the simulated cigarette; and
a latch being releasable by an inward movement of the drawer, whereupon the drawer is unlatched and urged by the resilient member to the opening position, and the latch being automatically engagable upon closure of the drawer to hold the drawer in a closed position against the action of the resilient member.

An example of a simulated smoking device and a refill device in accordance with the present invention will now be described with reference to the accompanying drawings, in which:

FIG. 8b is a detailed view of part 'b' of FIG. 8a;

FIG. 9 is an exploded perspective of the refill device of the second example.

Figure 1:
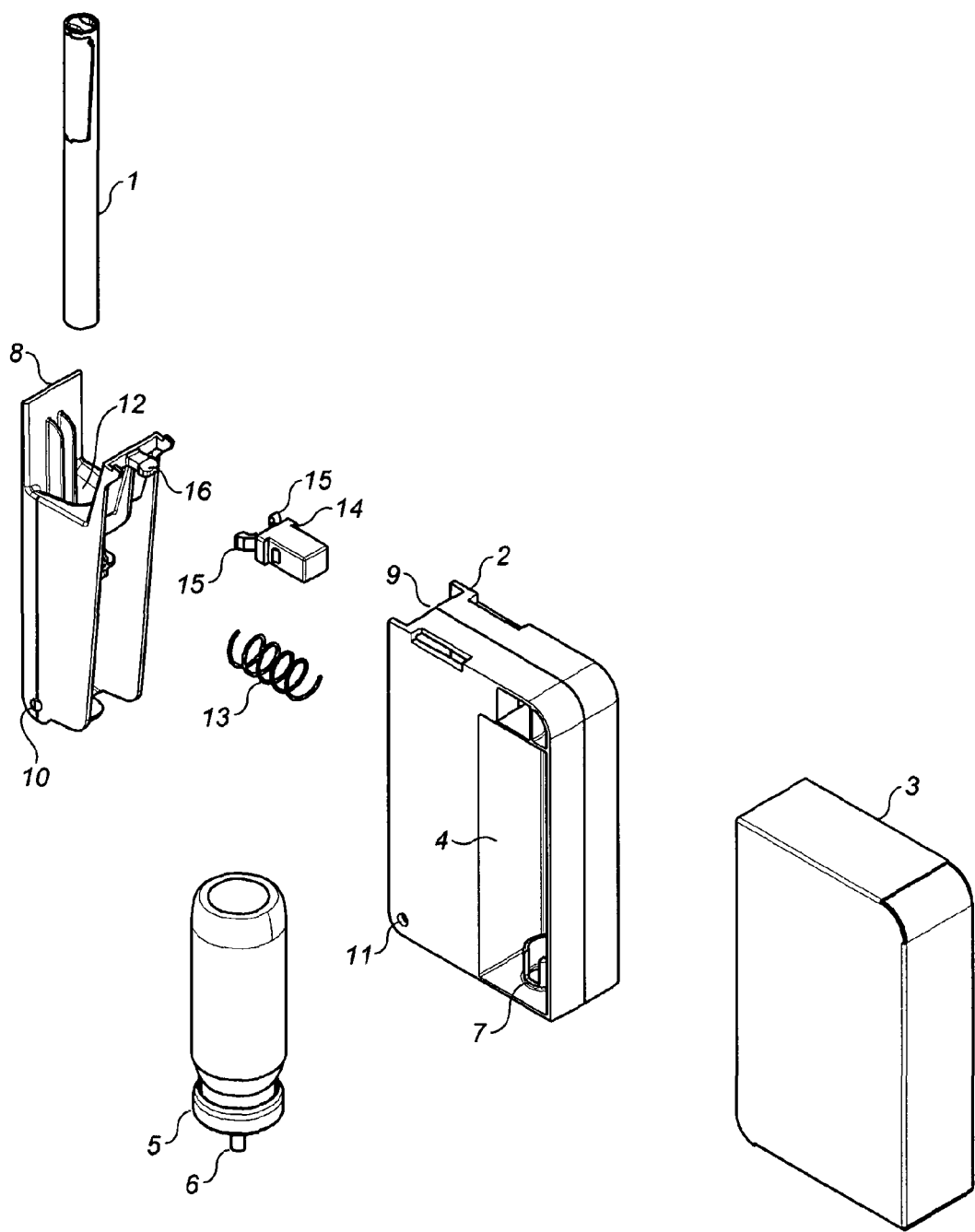
FIG. 1 is an exploded perspective view of the refill device and simulated cigarette.
Figure 2:
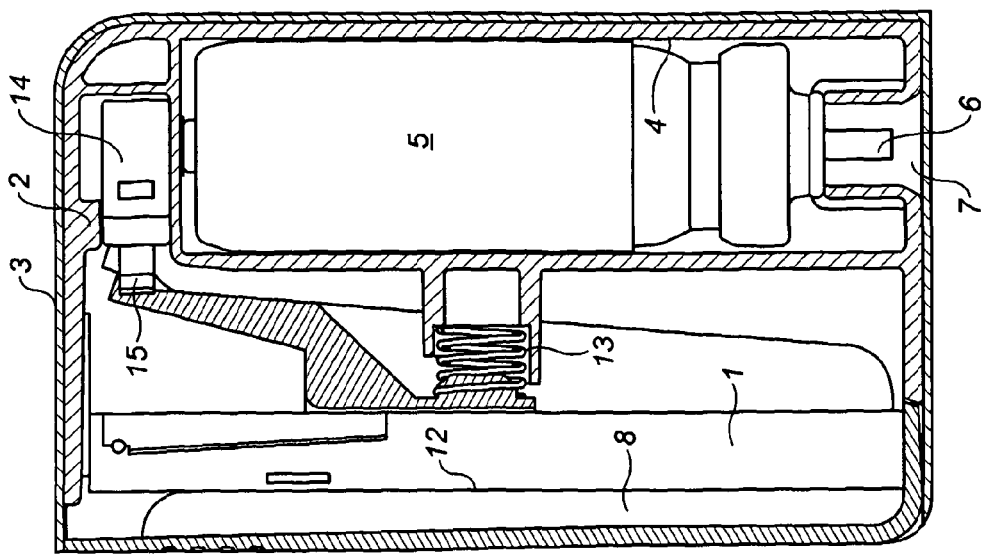
FIG. 2 is a cross-section of the refill device and simulated cigarette showing the drawer open.

Many of the details of the device are the same as those disclosed in WO 2009/001078 and these will not be repeated here. In particular, the structure of the simulated cigarette device, the dimensions, pressures, capacity and composition for the simulated cigarette device and refill device, and the nature of the refill canister, valve and refill method are as described in the earlier application.

The improvement resides in the nature of the arrangement to access the simulated cigarette and this is described below.

The simulated smoking devices comprises a simulated cigarette 1 which is as described in WO 2009/001278 and will not be described further here. Further modifications to the simulated cigarette device are disclosed in our own earlier applications PCT/GB2010/001487 and PCT/GB2010/001488.

The remainder of the simulated smoking device is the refill device. This comprises a main housing portion 2 which is a plastics moulding. This is surrounded by a thin card sleeve 3 on which is printed various information such as promotional information. The size of the housing is preferably similar to the size of a cigarette pack and may be adjusted to suit particular sizing formats, e.g., to be the size of a pack of 10 or 20 cigarettes. The housing 2 has a recess 4 in which is contained refill canister 5 of pressurised refill gas. The canister 5 has an outlet nozzle 6 at its lowermost end. With the canister 5 in the recess 4, the nozzle 6 sits above refill outlet orifice 7. The simulated cigarette device 1 is refilled by being pressed against the refill outlet orifice 7 as described in WO 2009/001078.

In general terms, the housing 2 is divided into two halves with one half containing the refill gas canister 5 and the other part containing a drawer 8 for the simulated cigarette device. This drawer 8, together with the manner in which it is mounted and operated will now be described.

The housing 2 has an opening 9 which extends along the full length and width of the side of the housing opposite to the side in which the refill gas canister 5 is mounted. This creates a hollow recess in which the drawer 8 is mounted.

Figure 3:
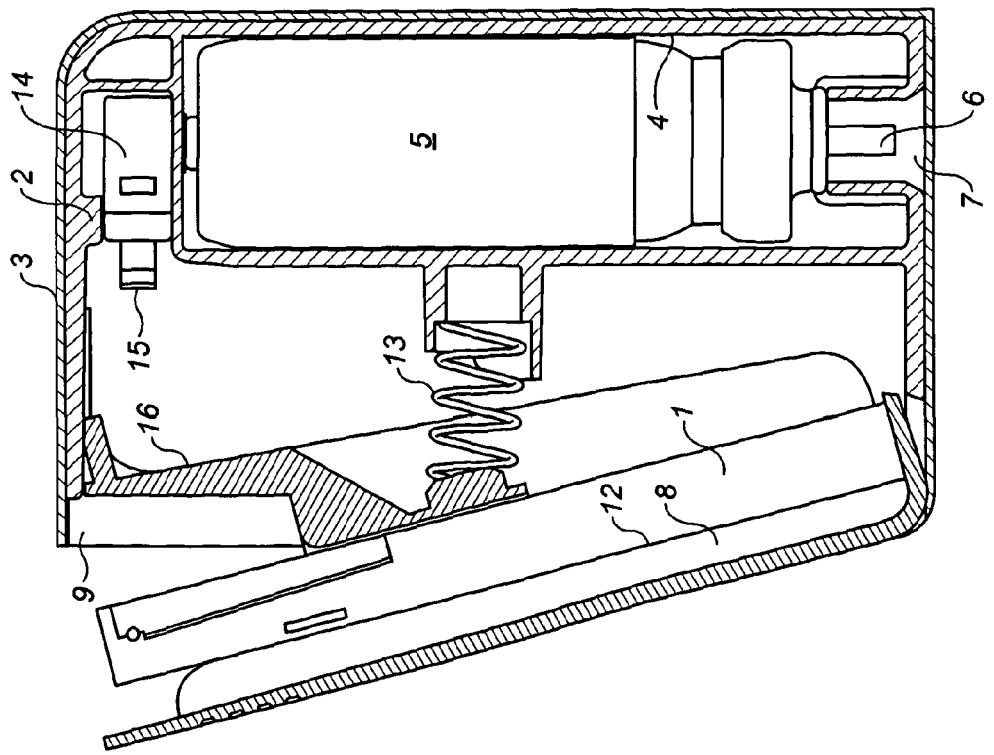
FIG. 3 is a view similar to FIG. 2 showing the drawer closed.

The drawer 8 has a pair of projecting lugs 10 (only one of which is shown) in FIG. 1 which engage with corresponding holes 11 (only one of which is shown in FIG. 1) in the housing 2 in order to provide a pivotal mounting for the drawer 8 in the housing 2. The drawer 8 defines a recess 12 for retaining the simulated cigarette 1. A spring 13 is mounted between the drawer 8 and the housing 2 so as to be compressed in the closed state as shown in FIG. 3 to urge the drawer 8 outwardly into an open position in which access to the simulated cigarette 1 is provided for a user. The drawer 8 is held in the closed position by a latch 14 mounted in the housing 2 above the canister 5.

The latch 14 is known, among other things, as a "mini-touch latch" and is well-known in the art. Essentially, the latch 14 has a pair of jaws 15 which engage with a tongue 16 on the drawer 8. In the closed position shown in FIG. 3, the jaws 15 engage with the tongue 16 to latch the drawer closed. In order to release the drawer, it is initially pushed inwards slightly causing the tongue 16 to be pushed deeper into the jaws 15. The tongue 16 has a flared shape which pushes on the jaws 15 forcing them apart. The jaws 15 release their grip on the tongue 16 and the spring 13 urges the drawer to the open configuration. The opening operation can be readily performed with one hand. The user then takes the simulated cigarette and, if necessary, presses it against the nozzle 6 in order to refill it.

Once they have finished using the simulated cigarette, they replace it in the recess 12 and push the drawer closed whereupon the jaws 15 engage with the tongue 16 to latch the drawer in the closed position. This closing operation can simply be carried out by the hand in which the refill is being held.

A second example is shown in FIGS. 4 to 9. Most of the features are the same as the first example. The significant change is that a new latch mechanism 19 is integrated into the refill device without the need for the 'mini-touch' latch component. In this way, a series of features can be engineered into the refill device housing so that the same function is provided as the mini-touch latch but there is a reduction in the number of components in the system.

Figure 5:
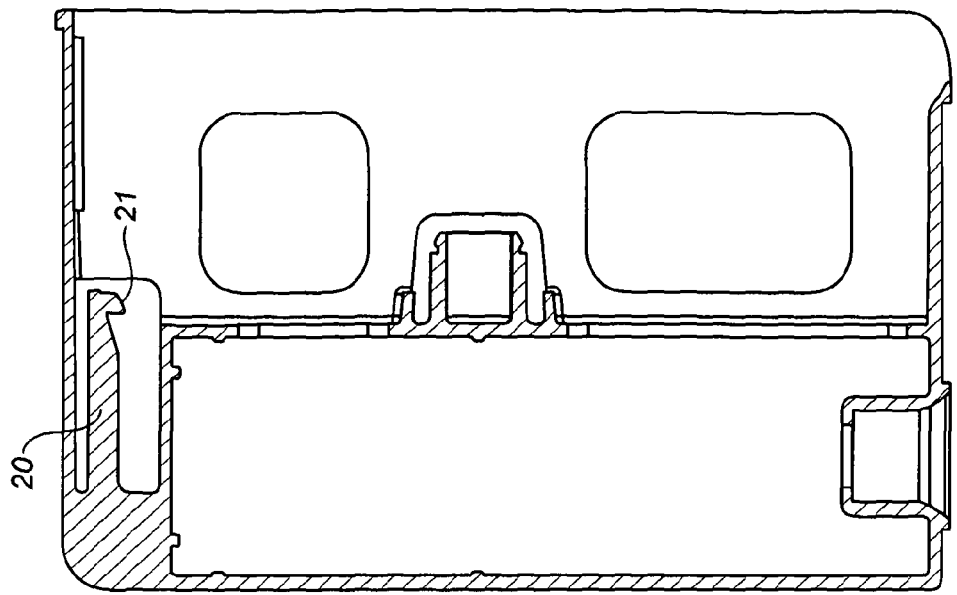
FIG. 4 and FIG. 5 are a cut-away side view of one side and a cross-section of an opposite side respectively of a housing of a second example of a refill device with the drawer closed.
Figure 4:
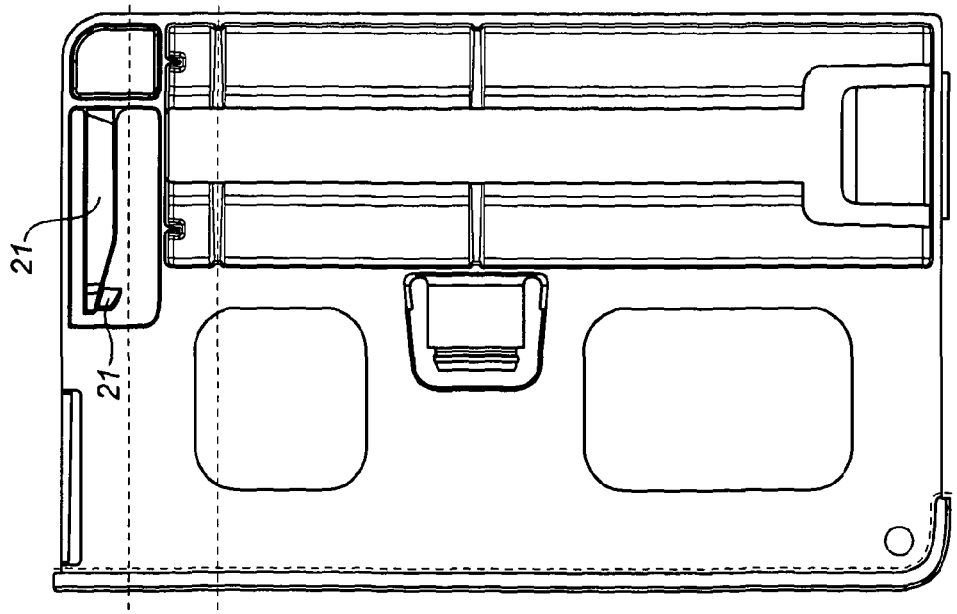
Figures 6, 7:
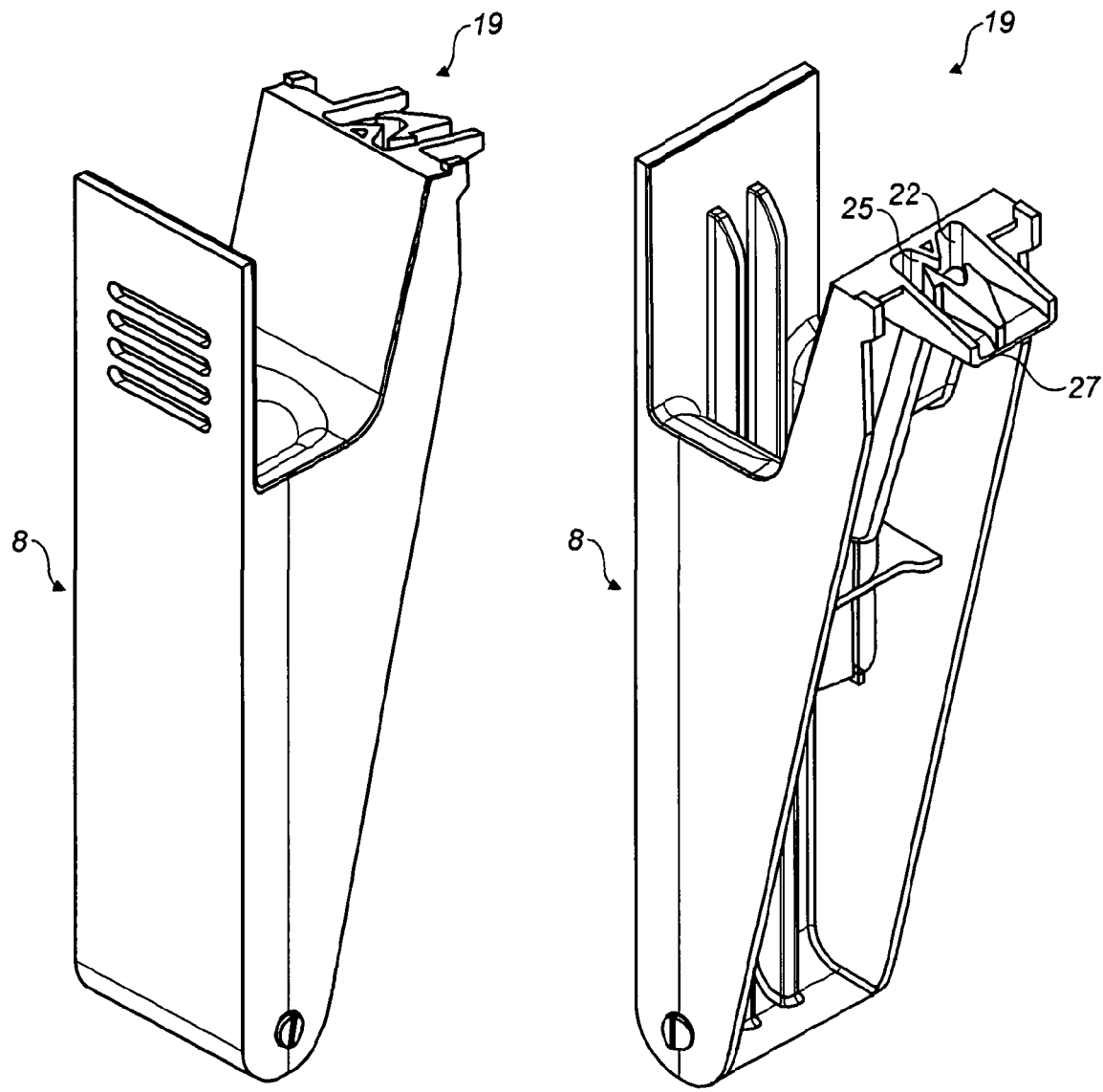
FIG. 6 and FIG. 7 are perspective views from opposite sides of the drawer mechanism of FIGS. 4 and 5.
Figure 8A:
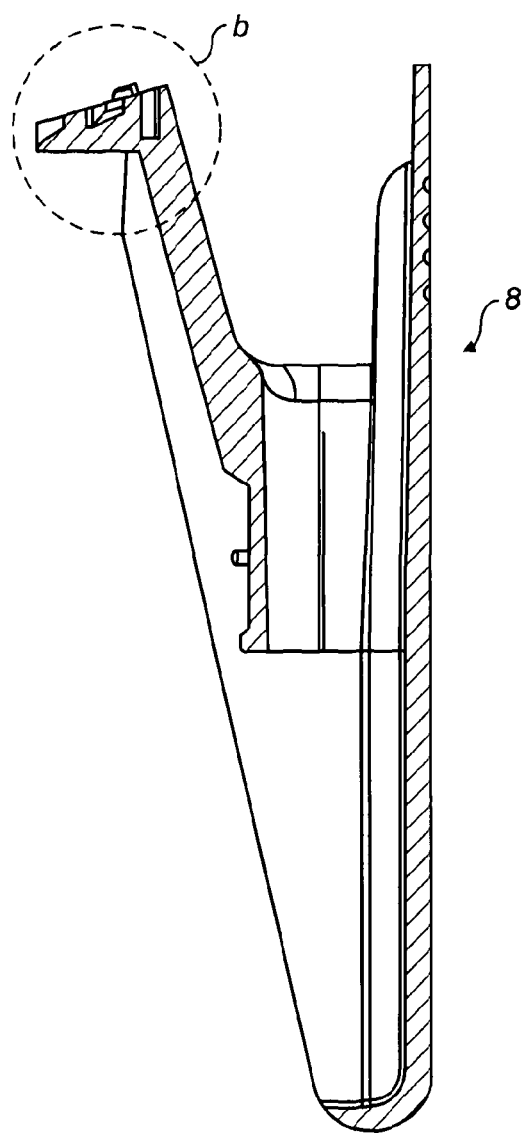
FIG. 8a is a cross section of the drawer of the second example.
Figure 8B:
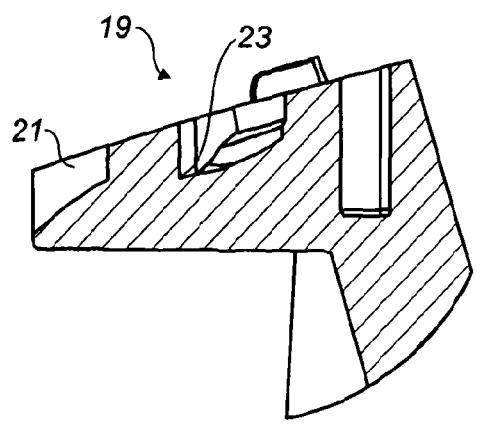
Figure 8C:
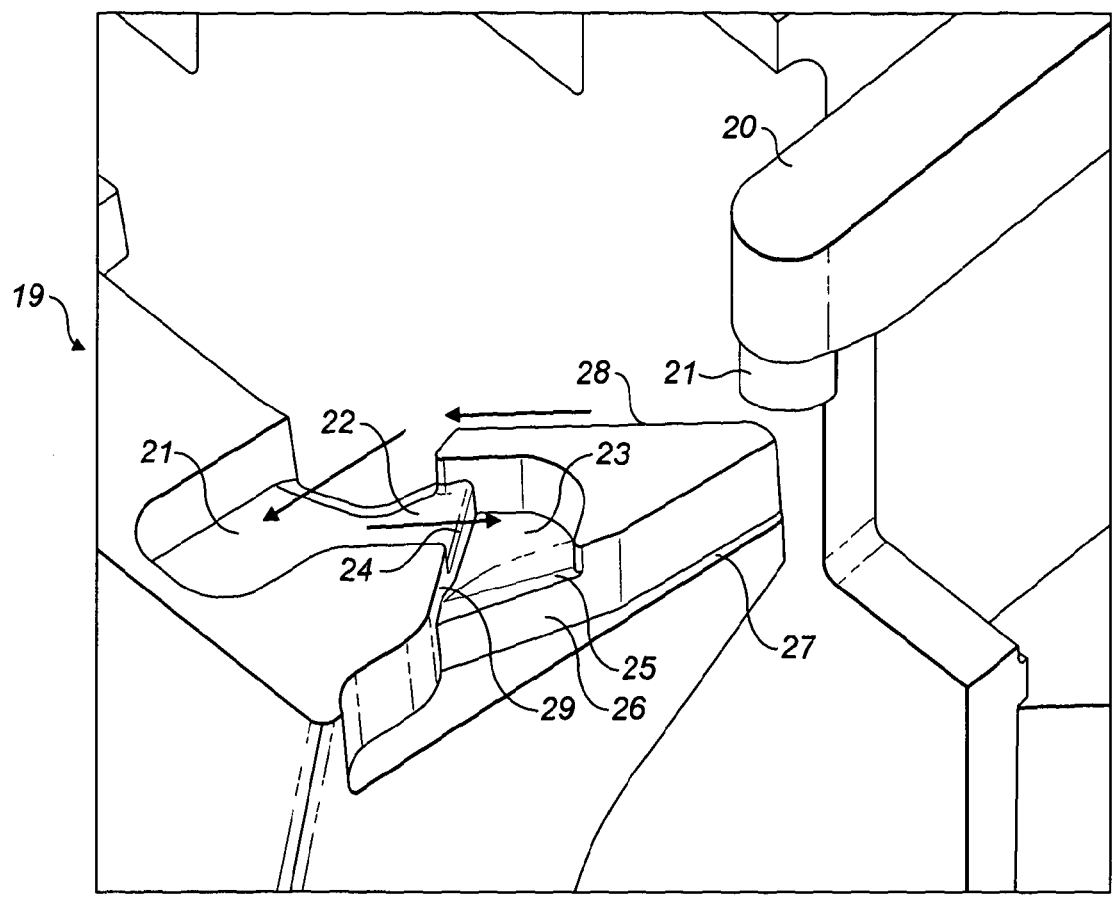
FIG. 8c is a perspective view of the travelling path of the latch mechanism of the second example.

As shown in FIGS. 4 and 5 the housing 2 has a protruding beam 20 with an angled hook 21 that when in a closed position, engages with a travelling path on the drawer 8 as best shown in FIGS. 7 and 8c. The path consists of an inlet entry path 21 and inlet return path 22 leading to a latched position 23. The inlet return path is separated from the latched position by a first downward step 24. The outlet path from the latched position 23 consists of an outlet initiation path 25 leading to a second downward step 26. On the opposite side of the second step 26 is an outlet exit path 27. The inlet entry 21, inlet return 22, outlet initiation 25 and outlet exit 27 paths form a generally "M"-shaped path as best shown in FIG. 7.

Facing the angled hook 21 is an inlet cam face 28. An outlet cam face 29 is provided facing the latched position 23.

From the open configuration shown in FIG. 8c, as the user pushes drawer 8, the hook 21 initially encounters the inlet cam face 28 and is deflected sideways into the inlet entry path 21. As it passes the inlet cam face 28, the resilience of the beam 20 urges the angled hook 21 back against the direction in which it is deflected by the inlet cam face 28, such that it travels along inlet return path 22 dropping over the inlet step 24 and settling in the latch position 23. In order to open the drawer, the user again pushes the drawer 8 against the action of the spring 13. The presence of the first step 24 and the outlet cam face 29 causes the angled hook 21 to travel along the outlet initiation path 25 in the process dropping over the second step 26 and into the outlet exit path 27. As the user releases the drawer, the resilience of the spring will cause the hook 21 to travel along outlet exit path 27 thereby releasing the drawer 8. In the opening process, the beam 20 is deflected sideways by the first step 24 and the outlet cam surface 29. As it leaves the outlet exit path 27 it is deflected by its own resilience back into the position shown in FIG. 8c where it once again faces the inlet cam surface 28 so that it is in a position to be re-closed as described above.

Additionally, the refill hole 7 can be situated at the bottom or at the top of the refill device according to the particular format. Should the refill hole 7 become situated at the top, and the canister will be stored in an upright position, the latch mechanisms will be integrated further towards the drawer in order to allow sufficient space for the refill canister to reside.

The invention claimed is:

1. A simulated smoking device comprising a simulated cigarette having a substantially cigarette-like shape and a refill device, the refill device containing a canister of refill gas and having an outlet valve against which the simulated cigarette is arranged to be pressed to release gas from the canister into the simulated cigarette, characterised by:
   a drawer in the side of the refill device;
   a recess within the drawer to retain the simulated cigarette;
   a resilient member to bias the drawer into an open position to allow access to the simulated cigarette; and
   a latch being releasable by an inward movement of the drawer, whereupon the drawer is unlatched and urged by the resilient member to the open position, and the latch being automatically engagable upon closure of the drawer to hold the drawer in a closed position against the action of the resilient member.

2. A simulated smoking device according to claim 1, wherein the drawer is pivotally mounted about a bottom corner of the refill device.

3. A simulated smoking device according to claim 1, wherein the latch has a mechanical interference with the drawer to hold the drawer in the latched position.

4. A simulated smoking device according to claim 1, wherein the latch is integrally moulded with a housing of the refill device and the drawer.

5. A simulated cigarette according to claim 1, wherein the outlet valve is in the bottom surface of the refill device.

6. A refill device for a simulated smoking device, the refill device containing a canister of refill gas, and having an outlet valve against which a simulated cigarette is arranged, in use, to be pressed to release gas from the canister into the simulated cigarette; characterised by:
   a drawer in the side of the refill device;
   a recess within the drawer to retain the simulated cigarette, in use;
   a resilient member to bias the drawer into an open position to allow access to the simulated cigarette; and
   a latch being releasable by an inward movement of the drawer, whereupon the drawer is unlatched and urged by the resilient member to the opening position, and the latch being automatically engagable upon closure of the drawer to hold the drawer in a closed position against the action of the resilient member.

7. A refill device according to claim 6, wherein the drawer is pivotally mounted about a bottom corner of the refill device.

8. A refill device according to claim 6, wherein the latch has a mechanical interference with the drawer to hold the drawer in the latched position.

9. A refill device according to claim 6, wherein the latch is integrally moulded with a housing of the refill device and the drawer.

10. A refill device according to claim 6, wherein the outlet valve is on the bottom surface of the refill device.

* * * * *